United States Patent [19]

Hardwick

[11] 4,078,588

[45] Mar. 14, 1978

[54] SUCTION DEVICE FOR COLLECTING MINERAL SAMPLES

[76] Inventor: Jack Andrew Hardwick, 1985 Chemawa Rd., Salem, Oreg. 97303

[21] Appl. No.: 749,678

[22] Filed: Dec. 13, 1976

[51] Int. Cl.² .............................................. B65B 3/14
[52] U.S. Cl. ..................................... 141/59; 141/286; 141/392
[58] Field of Search .................................. 141/18–29, 141/286, 392, 1–12, 37–68, 285

[56] References Cited

U.S. PATENT DOCUMENTS

| 411,792 | 10/1889 | Eggers | 141/24 |
| 474,940 | 5/1892 | Barnes | 141/24 |
| 3,223,289 | 12/1965 | Bouet | 141/24 |

Primary Examiner—Houston S. Bell
Attorney, Agent, or Firm—Francis Swanson

[57] ABSTRACT

A manually operated suction device for collecting samples of solid particles from cracks and crevices in stream beds and the like is disclosed. The device includes a squeeze bulb, a transparent collection chamber, and a narrow collecting nozzle for insertion into small openings. The device includes a plurality of curved baffles which direct collected material into the chamber and deter the material from escape back out of the collection chamber.

2 Claims, 3 Drawing Figures

SUCTION DEVICE FOR COLLECTING MINERAL SAMPLES

BACKGROUND OF THE INVENTION

1. Field of the Invention

This invention is directed to devices for collecting mineral samples and particulate matter from stream beds in general and more particularly to such devices which are manually operated and portable.

2. Description of the Prior Art

In collecting field samples of minerals and particulate matter from stream beds, gravel bars and the like a commonly used practice is that of "panning." With this technique the material of interest is placed in a shallow pan with a quantity of water and swirled or sloshed about. This causes the heavier material to settle to the bottom. These samples which settle out are then examined for the presence of precious metals such as gold or silver.

Other techniques used for larger scale examination include power dredging and sluicing. None of these techniques offer a convenient means of locating and retrieving samples from small cracks or crevices in the stream bed. Since heavy materials such as gold and silver bearing ores often settle out in such locations it is a matter of great interest to prospectors, geologists and others to be able to retrieve samples from such places.

SUMMARY OF THE INVENTION

It is the principal object of the invention to provide a means of readily retrieving samples of particulate matter from small or hard to reach locations in stream beds or other bodies of water.

It is a further object of the invention to provide a device which is readily disassembled for quick removal and examination of the retrieved material.

It is a further object of the invention to provide a light weight, portable device having a transparent collection chamber so that material may be examined as it enters the collection chamber.

It is a further object of the invention to provide baffle means within the sample collection chamber to deter the outward flow of previously collected material during successive cycles of operation during the collection process.

Other objects and advantages of the present invention will become more readily apparent with reference to the accompanying drawings and the following description.

DESCRIPTION OF THE PREFERRED EMBODIMENT

Figure 1:
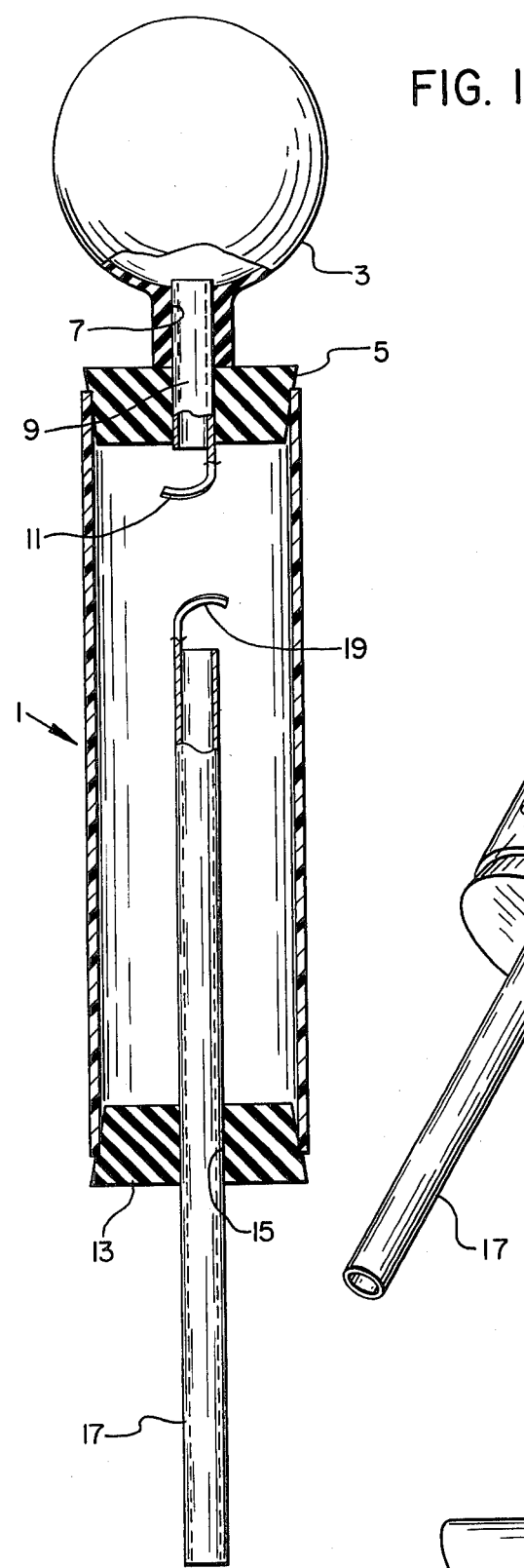
FIG. 1 is a side elevational view of the invention partially broken away to show the internal construction and relationship of the various components.

Referring now to FIG. 1, the invention comprises a relatively long tubular body 1. The body 1 is open at both ends and is transparent. It is preferably constructed of a highly resistant plastic such as polycarbonate.

At the upper end of body 1 there is inserted a squeeze bulb 3 having at its lower end a tapered plug 5. The bulb-plug is preferably constructed of an elastimer material for ready insertion and removal from the body 1. The bulb-plug contains a hollow passageway 7 into which is inserted a short hollow metal tube 9 having a curved baffle 11 at its lower end.

At the opposite end of body 1 there is inserted a tapered elastimer plug 13. Plug 13 has a hollowed passageway 15 into which is inserted a long narrow metal collecting nozzle which is hollow and has at one end a curved baffle 17.

OPERATION

The device is assembled as shown in FIG. 1. Assume now that the user wishes to take a sample of particulate matter from a narrow crevice in a stream bed. Bulb 3 is first squeezed. This action drives the air from the interior of the bulb. The lower end of nozzle 17 is then inserted into the crevice and the squeezing pressure on the bulb 3 is released. Bulb 3 will now expand creating sucking action which will draw water and particulate matter upward through the hollow interior of nozzle 17. The upward rushing water and sample material impinge on the curved inner edge of baffle 19 which directs the flow abruptly outward at right angles to the longitudinal axis of nozzle 17 where the stream containing the sample material will impinge on the wall of body 1. The particulate matter which is entrained in the stream of inflowing water, being heavier than the water, will settle downward within the collector chamber and finally rest on the inner surface of plug 13. This cycle can be repeated again and again until the user, viewing the amount of material collected through the transparent walls of body 1, is satisfied that he has recovered the amount he wishes.

Note that curved baffle 11 which is associated with the squeeze bulb 3 directs air squeezed from the bulb outward against the walls of body 1 thereby reducing any turbulence induced in the collected fluid and particulate samples. At the same time baffle 11 effectively deters entrance of particulate matter into the inner chamber of bulb 3 as the bulb expands during the intake cycle. As previously noted, baffle 19 directs the incoming fluid and sample material outward against the wall of body 1 so that it can float downward into the bottom of the collection chamber.

Figure 2:
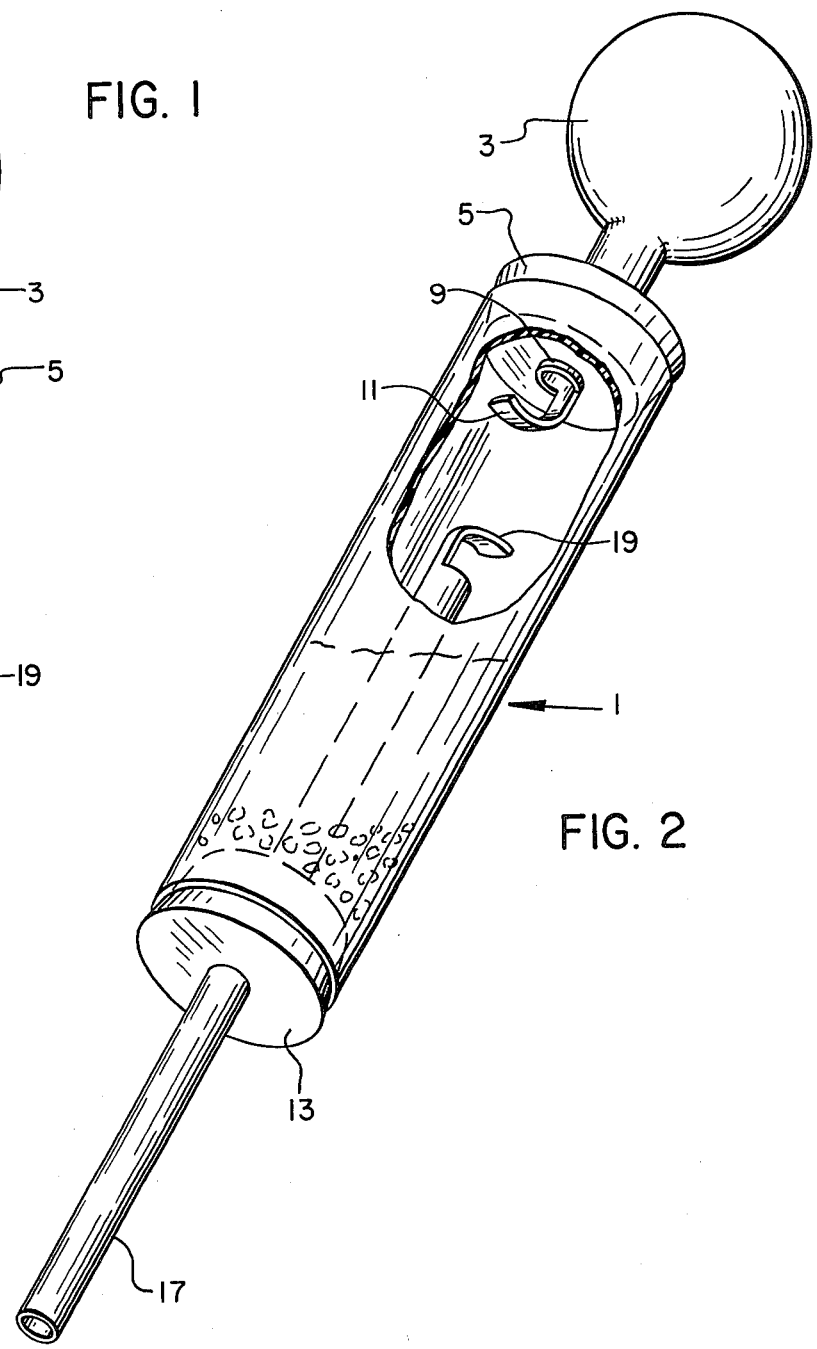
FIG. 2 is a perspective view of the invention partially broken away to show the relative relation of the internal baffles.
Figure 3:
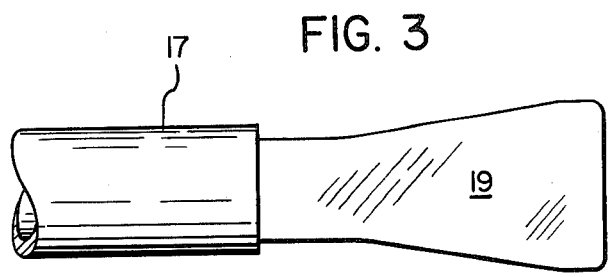
FIG. 3 is a plan view of the upper end of the suction nozzle showing the construction of one of the baffles.

As shown in FIG. 2 it is preferable to keep the level of water in the collection chamber below the upper end of nozzle 17 and baffle 19. This will effectively prevent escape of previously collected materials.

After the user has collected the amount of materials which he desires he need only remove plug 13 from the lower end of body 1 and empty the collected sample material into a suitable receptacle. The device can then be washed out with water from the stream and plug 13 reinserted. The device is now ready to be used again to collect new samples.

While specific embodiments of the invention have been shown and described in detail to illustrate the application of the inventive principles, it will be understood that the invention may be embodied otherwise without departing from such principles.

What is claimed is:

1. A particle collecting device comprising:
   an elongate hollow body;

a compressible member attached to one end of the hollow body for producing a suction force within the body;

a curved baffle attached to the compressible member for directing fluid toward a wall of the body;

an elongate hollow collecting nozzle mounted within an annular plug, the nozzle having a curved baffle at one end for directing fluid and particles drawn into the body toward a wall thereof;

the annular plug insertable within the body so that the curved baffle is contained within the body.

2. A particle collecting device comprising:

an elongate transparent body;

a hollow compressible bulb for producing a suction force within the body, the bulb inserted in one end of the body and having a curved baffle for directing fluid from within the bulb against a wall of the body;

an elongate hollow nozzle of small diameter relative to its length, the nozzle having an annular compressible plug mounted thereon;

the nozzle having a curved baffle mounted on one end for directing fluid and particles drawn into the body toward a wall of the body;

a compressible plug insertable in one end of the body so that the curved baffle is contained within the body.

* * * * *